(12) United States Patent
Coyne et al.

(10) Patent No.: US 12,035,769 B1
(45) Date of Patent: Jul. 16, 2024

(54) PROTECTIVE PROSTHETIC SLEEVE

(71) Applicants: Olivia Coyne, Pittsburgh, PA (US);
Devon Kelly, Franklin, TN (US);
Colleen Bell, Milford, OH (US);
Lauren Cline, South Bend, IN (US)

(72) Inventors: Olivia Coyne, Pittsburgh, PA (US);
Devon Kelly, Franklin, TN (US);
Colleen Bell, Milford, OH (US);
Lauren Cline, South Bend, IN (US)

( * ) Notice: Subject to any disclaimer, the term of this patent is extended or adjusted under 35 U.S.C. 154(b) by 104 days.

(21) Appl. No.: 17/718,030

(22) Filed: Apr. 11, 2022

(51) Int. Cl.
*A41D 27/12* (2006.01)
*A61F 2/50* (2006.01)
*A61F 2/64* (2006.01)

(52) U.S. Cl.
CPC .............. *A41D 27/12* (2013.01); *A61F 2/64* (2013.01); *A61F 2002/5001* (2013.01)

(58) Field of Classification Search
CPC ............ A41D 27/12; A61F 2002/5001; A61F 2002/607; A61F 2002/608; A61F 2/78; A61F 2/601; A61F 2/60; A61F 2/50; A61F 2005/0181
USPC ......................................................... 623/29
See application file for complete search history.

(56) References Cited

U.S. PATENT DOCUMENTS

2005/0240283 A1* 10/2005 Kania .................... A61F 2/7812
623/36
2015/0081038 A1* 3/2015 Rauch ...................... A61F 2/60
156/64

FOREIGN PATENT DOCUMENTS

TW          M527445 U   *  8/2016

OTHER PUBLICATIONS

GLT Products. Silicone/Fiberglass Cloth-Style 774. (Year: 2021).*

* cited by examiner

*Primary Examiner* — Christie Bahena
(74) *Attorney, Agent, or Firm* — Ference & Associates LLC

(57) ABSTRACT

An embodiment provides an apparatus for protecting clothing from damage caused by a prosthetic device, comprising: a base material comprising a plurality of vertical cuts; a protective material covering a front and a back of the base material; one or more structure bands weaved through at least a subset of the plurality of vertical cuts; a protective sheet overlaying the protective material on the back of the base material and along an upper portion of the apparatus; and two or more straps coupled to the apparatus, wherein each of the two or more straps comprise a mechanical mechanism for securing the apparatus when worn by the user.

19 Claims, 7 Drawing Sheets

PROTECTIVE PROSTHETIC SLEEVE

BACKGROUND

In the United States, almost two million people are living with limb loss caused by vascular disease or trauma. Artificial limbs and prosthetics are used for treatment and fall into four main categories: transtibial, transfemoral, transradial, and transhumeral amputations. Transfemoral amputations occur from the hip the knee joint. In other words, the leg in amputated above the knee. Transtibial amputations occur from the knee to the ankle, or, in other words, below the knee. The transradial and transhumeral amputations are similar except for arms instead of legs. Two main classifications of artificial limbs are used: socket prosthetics or osseointegrated limbs. The socket prosthetics joins the residual limb to the prosthetic. The osseointegrated prosthetic require the bone of the amputated limb to grow around a metal implant and is surgically anchored to the limb. Therefore, the osseointegrated prosthetic cannot be removed. The socket prosthetic may be removed at any time. Each of these prosthetic types come with their own issues, but both also cause common problems amputees must face unbeknownst to society, such as interference with clothing that is worn.

BRIEF SUMMARY

One embodiment provides an apparatus for protecting clothing from damage caused by a prosthetic device, comprising; a base material comprising a plurality of vertical cuts; a protective material covering a front and a back of the base material, wherein the protective material allows access to the plurality of vertical cuts; one or more structure bands weaved through at least a subset of the plurality of vertical cuts; a protective sheet overlaying the protective material on the back of the base material and along an upper portion of the apparatus, wherein the protective sheet, when the apparatus is worn, contacts a portion of the prosthetic device worn by a user; and two or more straps coupled to the apparatus, wherein each of the two or more straps comprise a mechanical mechanism for securing the apparatus when worn by the user; wherein the securing the apparatus comprises wrapping one of the two or more straps around a lower portion of a limb of the user and wrapping another of the two or more straps around an upper portion of the prosthetic device worn by the user.

Another embodiment provides a device for protecting clothing from damage caused by a prosthetic device, the device comprising: a base layer comprising a plurality of cuts extending in a vertical direction from an upper portion of the base layer to a lower portion of the base layer, wherein the plurality of cuts do not extend from edge to edge; a first set of a plurality of strips of material located on a front side of the base layer, wherein each of the plurality of strips of the first set are positioned between two of the plurality of vertical cuts of the base layer; a second set of a plurality of strips of material located on a back side of the base layer, wherein each of the plurality of strips of the second set are positioned between two of the plurality of vertical cuts of the base layer; at least one support band weaved through the plurality of vertical cuts and positioned at a top of the plurality of vertical cuts; at least a second support band weaved through the plurality of vertical cuts and positioned at a bottom of the plurality of vertical cuts; at least a third support band weaved through the plurality of vertical cuts and positioned at a center position of the plurality of vertical cuts; at least one attachment mechanism positioned at an upper portion of the device, wherein the at least one attachment mechanism allows for attachment of the device to a limb of a user; and at least a second attachment mechanism positioned at a lower portion of the device, wherein the at least a second attachment mechanism allows for attachment of the device to a prosthetic of the user.

The foregoing is a summary and thus may contain simplifications, generalizations, and omissions of detail; consequently, those skilled in the art will appreciate that the summary is illustrative only and is not intended to be in any way limiting.

For a better understanding of the embodiments, together with other and further features and advantages thereof, reference is made to the following description, taken in conjunction with the accompanying drawings. The scope of the invention will be pointed out in the appended claims.

DETAILED DESCRIPTION

Figure 1:
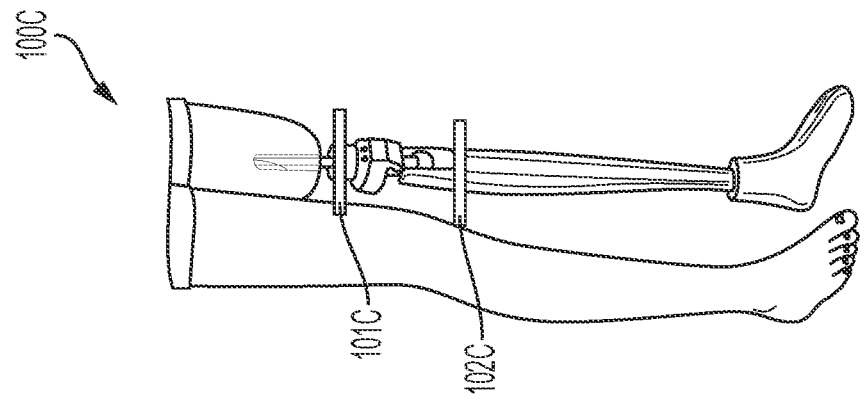
FIG. 1 illustrates an apparatus sketch and anchor positions for the knee sleeve.
Figure 1:
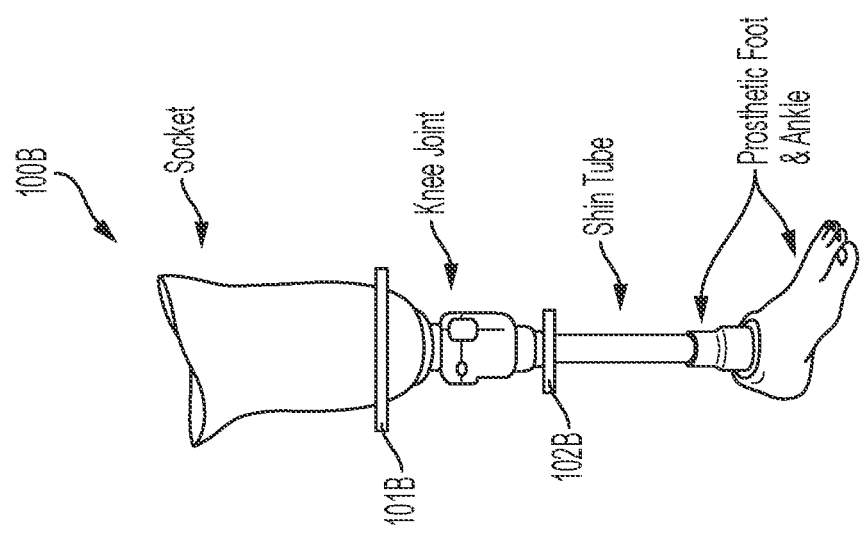
Figure 1:
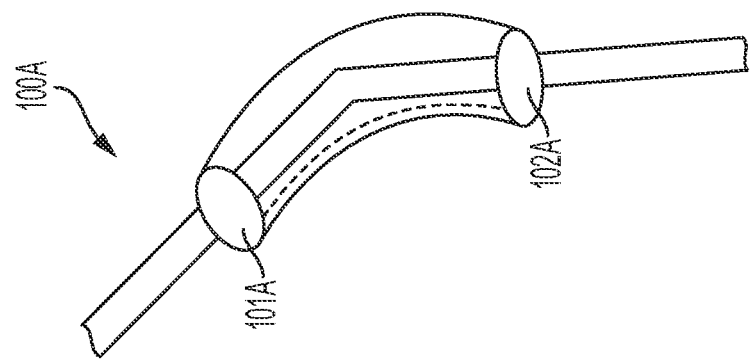

It will be readily understood that the components of the embodiments, as generally described and illustrated in the figures herein, may be arranged and designed in a wide variety of different configurations in addition to the described example embodiments. Thus, the following more detailed description of the example embodiments, as represented in the figures, is not intended to limit the scope of the embodiments, as claimed, but is merely representative of example embodiments.

Reference throughout this specification to "one embodiment" or "an embodiment" (or the like) means that a particular feature, structure, or characteristic described in connection with the embodiment is included in at least one embodiment. Thus, the appearance of the phrases "in one embodiment" or "in an embodiment" or the like in various places throughout this specification are not necessarily all referring to the same embodiment.

Furthermore, the described features, structures, or characteristics may be combined in any suitable manner in one or more embodiments. In the following description, numerous specific details are provided to give a thorough understanding of embodiments. One skilled in the relevant art will recognize, however, that the various embodiments can be practiced without one or more of the specific details, or with other methods, components, materials, et cetera. In other instances, well known structures, materials, or operations are not shown or described in detail to avoid obfuscation.

A leg amputation will be discussed herein as an example. However, it should be understood that similar problems and techniques occur with arm or other limb amputations. When transfemoral amputees wear long pants, pant material becomes entangled in the prosthetic knee. Sharp edges of the prosthetics tear through materials leading to pant destruction. Currently, solutions to this damaging process require amputees to take matter into their own hands. For example, duct tapping the pants, sewing on patches, or purchasing cheap pants and replacing them often. There are companies in which produce clothing in an attempt to overcome the damage caused by the prosthetics, usually by adding additional material or using material that is harder to damage. However, these articles of clothing are quite expensive.

Being that pants are an essential aspect of many wardrobes, the designed apparatus is aimed to be a cost-effective simple solution to mitigate the effects of prosthetic damage on long pants. The described solution can also be modified to be used with other articles of clothing or prosthetics. In accordance with the present invention, an apparatus provides a knee brace or sleeve that an amputee may wear over a prosthetic and under a pair of pants or other article of clothing to assist in preventing the prosthetic from tearing or ruining the article of clothing. Additionally, the sleeve is designed so that it does not damage the article of clothing.

Prior to wearing the sleeve, the sleeve may be in a flat, open orientation, and including multiple parts that are designed to minimize the damage caused by the prosthetic on the article of clothing. Instead, the prosthetic touches the sleeve, thereby directing any damage caused by the prosthetic to the sleeve instead of the article of clothing. While the sleeve is open, the multi-layered, protective materials used in creating the apparatus are viewable in the inside portion of the sleeve. Starting from the inner most materials, the sleeve utilizes a base material that moves or stretches with the joint of an amputee, but provides a durable layer between the prosthetic worn by the amputee and the prosthetic. The flexible, durable base material may include a material that permits the user to be mobile without damaging, or reducing damage to, the sleeve.

To assist in not damaging the sleeve or brace, the base material is covered with a protective material to absorb the friction between the prosthetic and the sleeve. This protective material covers the base material, acting as a second layer of durability across the sleeve. The protective material covers both sides of the sleeve, and is joined to the base material in such a way to increase durability of the sleeve while also permitting motion of the joint of the prosthetic or person wearing the prosthetic. Since the sleeve or brace is meant to be worn while a user is walking, one or more structure or support bands may be included to assist with securing the sleeve to a single position while being worn, and provide an additional, reinforced center portion of the sleeve. The structure or support bands are integrally coupled to the sleeve by being weaved through the protective material and base material to ensure a secure grip on the user's limb area that does not slip or separate while the user is mobile. The structure or support bands are made from a durable material that can absorb the friction caused between the prosthetic and the sleeve and not tear.

The protective material and the structure bands are viewable on both sides of the apparatus when it is in an open position. Further, while the sleeve is open, a protective sheet is viewable overlaying the protective material along the upper portion and the inside of the sleeve. For ease of readability, the upper portion will refer to the portion of the apparatus that is the top half when the sleeve is being worn. Thus, when closed, the upper portion is the part of the sleeve that contacts the amputee's leg or socket and contacts the upper edges of the amputee's prosthetic. The protective sheet is made from a durable material that can withstand force and the friction caused by the rubbing of the prosthetic against the sleeve, thereby protecting the clothing worn over the sleeve. The protective sheet may be orientated in such a way that, when properly worn, the protective sheet absorbs the majority of friction caused by the movement of the prosthetic joint instead of the clothing of the user.

The sleeve also includes the use of straps integrally coupled to the sleeve to assist with securing the sleeve in place while a user is mobile. These straps may be located in two or more locations of the joint region of the user, and may be maintained in place using a mechanical mechanism to ensure the sleeve does not come loose while in use. The mechanical mechanism is integrally coupled to the straps and keeps the sleeve closed while worn by a user. The two or more locations may include a location along the top of the sleeve and the along the bottom of the sleeve. Along the top of the sleeve, the strap may be wrapped around the lower most portion of the amputee's limb or socket. The correct location of the wrapped, upper strap of the sleeve includes securing the sleeve to the leg of the user, and further includes the alignment of the protective sheet over the edges of the prosthetic that may damage a user's clothing. As for the lower strap of the sleeve used to secure the sleeve, the strap is wrapped around an upper portion of the user's prosthetic, but below the joint region of the prosthetic. The securing of the sleeve to the prosthetic minimizes potential sliding-down of the sleeve while the user is in motion. Being that the lower strap is wrapped around a portion of the prosthetic, and the upper strap is wrapped around a lower portion of the user's leg or socket, the wrapping of the lower strap of the knee is tighter and more narrow since the diameter of the prosthetic is much less than the diameter of the user's leg. The integrally coupled mechanical mechanism is used to connect the straps back onto the sleeve, negating any hanging or swinging material that may influence the mobility of the user.

The illustrated example embodiments will be best understood by reference to the figures. The following description is intended only by way of example, and simply illustrates certain example embodiments.

The device is a limb sleeve to be worn by an amputee over a prosthetic worn by the amputee and beneath an article of clothing worn by the amputee. The device, therefore, provides a protective sleeve between the prosthetic joint of the amputee which has rough edges, and the clothing worn by the amputee. The sleeve may minimize or negate the tearing and ripping of the user's clothing which traditionally occurs when amputees wear clothes over the prosthetics and engages in activities that put the prosthetic in motion. The example that will be used here throughout is the example of a knee sleeve over a prosthetic leg having a knee joint. However, this is not intended to limit the scope of this disclosure to a knee sleeve and knee prosthetic as it is apparent that the device could be modified to be worn over a different limb, for example, an arm and elbow joint.

Additionally, for ease of readability orientation directions will be defined herein. However, these are only intended to provide directions for understanding and are not intended to limit the scope of this disclosure. The term "upper" or "top" will refer to the portion of the knee sleeve that is located at an upper portion of a limb when the device is worn, for example, the thigh side of the leg or bicep side of the arm. The term "lower" or "bottom" will refer to the portion of the device that is located at a lower portion of a limb when the device is work, for example, the calf side of the leg or forearm side of the arm. The term "front" or "inside" will refer to the side of the device that will touch the limb and/or prosthetic. In other words, the front or inside will be not visible when the device is worn. The term "back" or "outside" will refer to the side of the device that will not touch the limb and/or prosthetic. In other words, the back or outside will be the visible side when the device is worn. The term "vertical" will refer to a direction that runs from the top to bottom of the device, and generally follows the narrow direction of the device. The term "horizontal" will refer to a direction that runs from one side of the device to the other side of the device, and generally follows the wider direction of the device. For illustration, the device will be worn in a manner that the device is wrapped around the limb along the horizontal orientation, meaning the device will bend across the horizontal orientation.

When not being worn and is in an open orientation, the knee sleeve may be a flat, rectangular apparatus with two or more attachment straps, at least one of which is coupled along the upper portion of the sleeve and another of which is coupled along the lower portion of the sleeve. The upper and lower portions are with respect to the long sides of the rectangular shape of the open knee sleeve. The flat orientation of the open sleeve may permit an easy operation of the knee sleeve when attempting to wear the knee sleeve. Unlike traditional knee region sleeves which require a user to put their leg through the sleeve (as if putting on a pant leg), this knee sleeve allows for the user to wrap the knee sleeve around the knee region, which further assists in properly aligning high-contact and high-friction areas with the appropriate parts of the apparatus, for example, aligning the protective sheet along the inside of the knee sleeve with the edges of the prosthetic that may damage the user's pants.

When put on and worn by the user, the knee sleeve may be worn in a cylindrical orientation that includes openings at each end of the cylinder when the sleeve is closed. These openings permit the wrapping of the sleeve around the outside of the knee joint region of the user. Being that the knee sleeve is a cylindrical shape when worn and comprises a hole at each end, the straps present along the top and bottom of the knee sleeve may be used to secure the knee sleeve in place, particularly when the user is in motion. As mentioned previously, being that the diameter of the prosthetic that a user is wearing is commonly much less than the diameter of the human leg, the lower wrapping of the strap may be tighter and more narrow in order to secure the knee sleeve in place, compared to the wrapping tightness and width of the upper strap wrapping the leg of the amputee.

The easy use and operation of putting on the knee sleeve using a wrapping method rather than attempting to push a prosthetic through a sleeve further permits an easy transition for removing the knee sleeve from being worn. Simply detaching the straps wrapped around the two or more locations present in the knee region will release the knee sleeve from surrounding the knee region formed between the amputated leg of the amputee and their prosthetic. In addition to the non-traditional method of putting on and taking off of the sleeve, the apparatus is designed in a manner that includes additional aspects that are included with conventional techniques for reducing damage to clothing from prosthetics, as described further herein.

Referring to FIG. 1, the figures present within FIG. 1 illustrate an example location in which a user may wear a prosthetic, and additionally illustrates two anchor points of the knee sleeve with respect to a lower leg amputation type prosthetic. 100A depicts a rough sketch of the apparatus when worn by a user. As can be seen in 100A, the knee sleeve includes an opening along the upper portion of the knee sleeve 101A, and an opening along the lower portion of the knee sleeve 102A. As one can imagine, if a user were to attempt to slide the prosthetic leg through the sleeve, the joint in the knee region would make such a sliding into and through the sleeve difficult. Additionally, the friction caused by sliding the sleeve on a off for each wearing adds additional wear to the sleeve.

In 100B, the figure shows a standard system for a prosthetic attached to the user's amputated leg using a socket prosthetic method. As can be seen in 100B, the knee joint is present between the amputated portion of the user's leg (and socket) and the shin of the prosthetic, and it is in this region that the knee sleeve may be applied to cover the knee region. 101B shows the location of the upper anchor position of the knee sleeve, and the lower anchor position is shown at 102B. The upper position 101B shows that in a socket prosthetic system in which the amputated leg is placed in a socket and worn (not integrally coupled to the human leg), a portion of the sleeve may be wrapped around the socket portion. As for the lower position 102B, the anchor position may be located on shin of the prosthetic. Thus, the knee joint area is still defined by the area between the amputee's leg and their prosthetic.

In 100C, the figure shows the region in which the knee sleeve may cover with respect to a system that utilizes osseointegrated prosthetics. The location of the upper anchor position 101C is once again shown to be present above the knee joint region. 102C shows the lower anchor position for the knee sleeve device. The osseointegrated prosthetic system does not use the socket approach, as illustrated in 100B, but rather is integrally coupled to the human leg. Thus, when anchoring the upper position 101C, the upper strap may make direct contact with the user's leg. Establishing the appropriate anchor points for the straps to be wrapped around and thereafter secured to the user of the knee sleeve is important when attempting to maximize the success of the absorbance of friction at the knee sleeve, and minimizing the damage to the pants of the user. Additionally, it is shown that the knee sleeve can be utilized with at least any of the main types of prosthetics.

Figure 2:
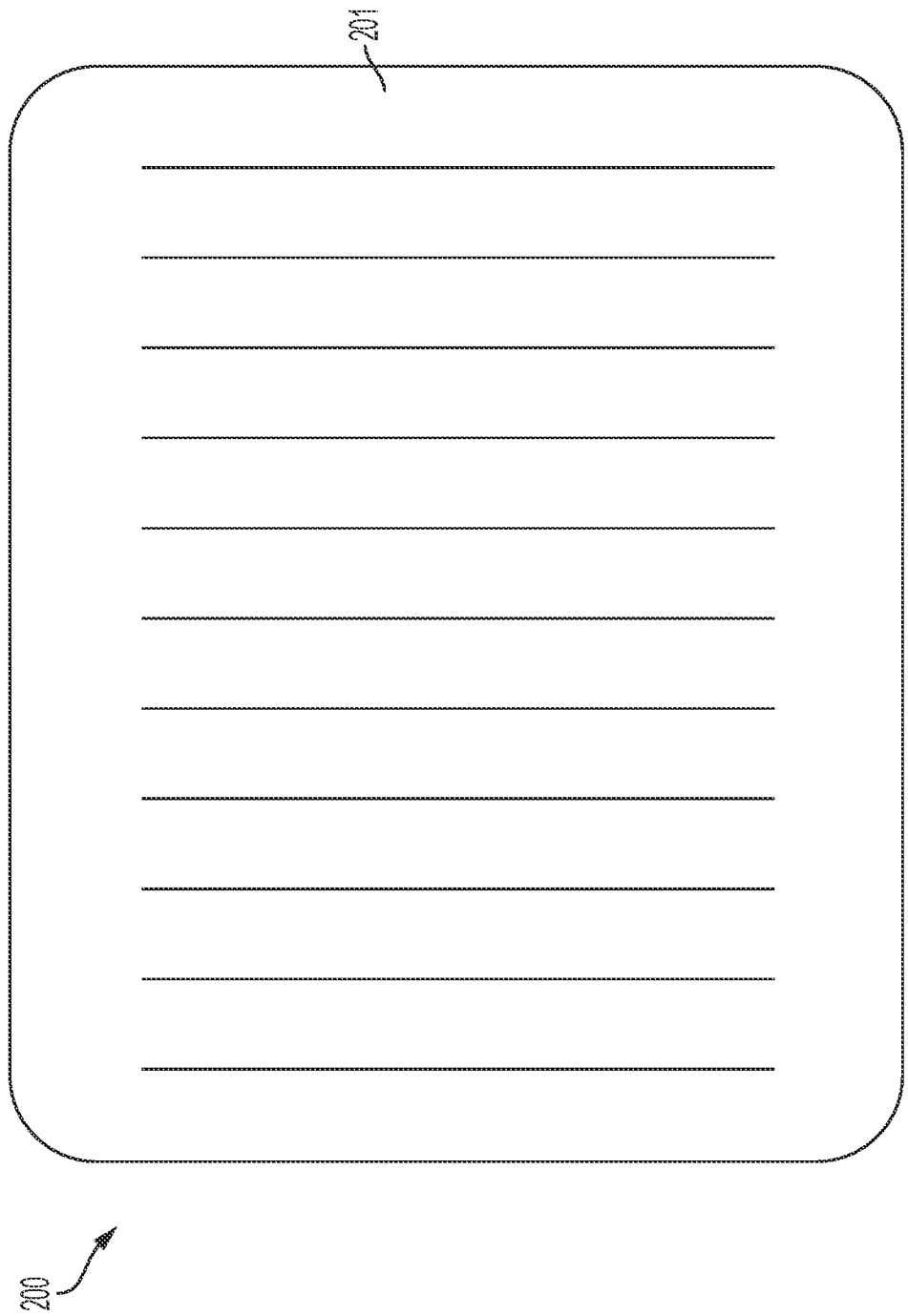
FIG. 2 illustrates an example base material sketch.

The knee sleeve device may be designed to maximize durability while simultaneously providing seamless wearing of the device. In other words, the knee sleeve is designed in a way that when worn by the user, the user will not notice the knee sleeve is being worn or will at least minimally notice the knee sleeve. This combination of durability and comfort for the user starts with the determination and utilization of a base material. FIG. 2 illustrates an example sketch of the base layer. The base layer is generally rectangular in shape with the long sides across the upper and lower portions and the short sides along the sides of the layer. The horizontal direction follows the direction of the longs sides and it is in the horizontal direction that the knee device is wrapped around the joint area of the user. Thus, the horizontal dimension of the base layer is of a size to allow for wrapping around the limb of a user, for example, 12 inches, 18 inches, or the like. The vertical dimension follows the direction of the short sides. Thus, the vertical dimension of the base layer is of a size to allow covering of both the leg of the user and the prosthetic, for example, 10 inches, 12 inches, or the like. In order to allow for unrestricted movement, the layers may be thin. Thus, the thickness of the base layer may be minimal and measurable in millimeters or parts of millimeters. The provided dimensions are merely illustrative and not intended to be limiting as other dimensions may be useful for different users, limbs, and the like.

The base material is the starting layer of the knee sleeve device, meaning that the other materials and/or layers are added to the base material to create the knee sleeve device. At 200, a base material sheet is provided. In an embodiment, the base material of the sheet may be any material that promotes mobility, and is durable enough expand and contract with user leg motion without damage, as well as provide an initial layer for additional portions of the knee sleeve to be coupled. The base material is the main piece of structure for the knee sleeve apparatus. Thus, the material used must be able to withstand the stress of leg movement. In an embodiment, the base material layer 200 is made of polypropylene. Polypropylene is a durable plastic material that permits expanding and contracting. Polypropylene may withstand levels of friction and may not drastically stretch out over time, permitting consistent use of the knee sleeve without the worry of stretching and potentially not fitting over time.

The base layer may also include slits or cuts 201. These cuts extend in the vertical direction of the base layer form an upper portion of the base layer to the lower portion of the base layer. As illustrated in FIG. 2, the cuts do not extend from upper edge to lower edge. In other words, the cuts or slits do not remove a piece of the base material from other pieces of the base material. The slits or cuts are provided to assist with the mobility of the sleeve and allow for a larger range of leg motion. Additionally, the cuts are used to connect some other pieces to the sleeve as described further herein. The number of slits may vary and may be selected based upon the application and may be selected to optimize the mobility against the stability of the device.

In an embodiment, the base material 200 may include a mesh pattern. A mesh pattern may make the base material lighter and increase maneuverability. Being that a mesh pattern permits gaps in the material, the weight of the base material may decrease. For example, a full sheet of a polypropylene base material will weigh more than a polypropylene sheet with a mesh pattern since the full sheet includes more material. Additionally, the gaps present in the material in the mesh pattern permit a larger range of motion since there is more space for the polypropylene to move. In an embodiment, the base material sheet may be cut into strips to permit even more mobility; however, cutting the base material sheet into strips may decrease the durability and structure of the knee sleeve. Additionally, by cutting the base material into strips the time to manufacture the device increases.

The base material may then be covered by a protective material to increase durability and structure of the knee sleeve worn by the user. Additionally, the protective material is used to cover any sharp edges of the base layer. The protective material used may be required to be durable against friction caused by the rubbing of a prosthetic against the material. This protective layer covers both sides of the base material. Both the front and back of the knee sleeve utilizes the protective material since friction occurs both inside the knee sleeve when worn (friction between prosthetic and knee) and on the outside of the knee sleeve (friction between the knee sleeve and pants). In an embodiment, in addition to being a durable material, the protective material used to overlay the base material may further permit mobility. A system may not use a protective material that is stiff, though tough, since the user will be walking and performing other leg movements while wearing the knee sleeve. Mobility and flexibility are both important traits when selecting the protective material, for the protective material will be the material used most across the knee sleeve, and must not restrict an amputee more than their injury already has.

Thus, the protective material may be fabric (e.g., flannel, cotton, fleece, etc.), lightweight flexible rubber, and the like. In one embodiment, the protective material is bias tape. Bias tape is a durable yet flexible material that permits motion while remaining intact when influenced by friction. Since bias tape is generally material that is cut on the bias, meaning it is cut at an angle across the grain, the material is more resistant to wear. The protective material may be cut into strips that are then placed or positioned between the cuts of the base layer on both the front side and the back side of the base layer. Thus, the strips may be of a width that matches the spacing between the cuts. Accordingly, the sleeve may include two sets of a plurality of strips, with one set being applied to the front of the base layer and another set being applied to the back of the base layer. The sleeve may also include a third set of protective material strips. These may be positioned through the cuts of the base layer such that part of the protective strip is located on the front side of the base layer and another part of the protective strip is located on the back side of the base layer. In other words, the protective strip may be like a taco shell with the base layer and the other protective strips located within the taco shell. This helps prevent rough edges of the base layer from being exposed and also provides a cleaner appearance and provides some added structure and support. This can be seen in FIG. 4, where the lighter areas 402 are the first/second set of strips and the darker areas 402 are the third set of protective strips that are located within the cuts and wrapped around the edges of the base layer. The protective material, whether a single piece of material, strips of material, or the like, are secured and coupled to, for example, via sewing or other mechanical connection means, the base layer.

To assist with the structure and durability of the knee sleeve when worn by a user, the knee sleeve may include structure or support bands 403 weaved through the protective material and base material. One or more structure or support bands may provide a backbone-like structure support to the knee sleeve that runs in the horizontal direction of the sleeve. The structure bands may be made from a durable material that may expand and contract with the motion of the user's knee region and leg, which allows for movement of the sleeve with movement of the user but ensuring that the position of the sleeve does not move. Additionally, since these run in the horizontal direction they provide a structural foundation that increases a strength of the structural foundation for the knee sleeve. Thus, the structure bands assists the knee sleeve in maintaining its shape and providing a strength to the sleeve.

Figure 4:
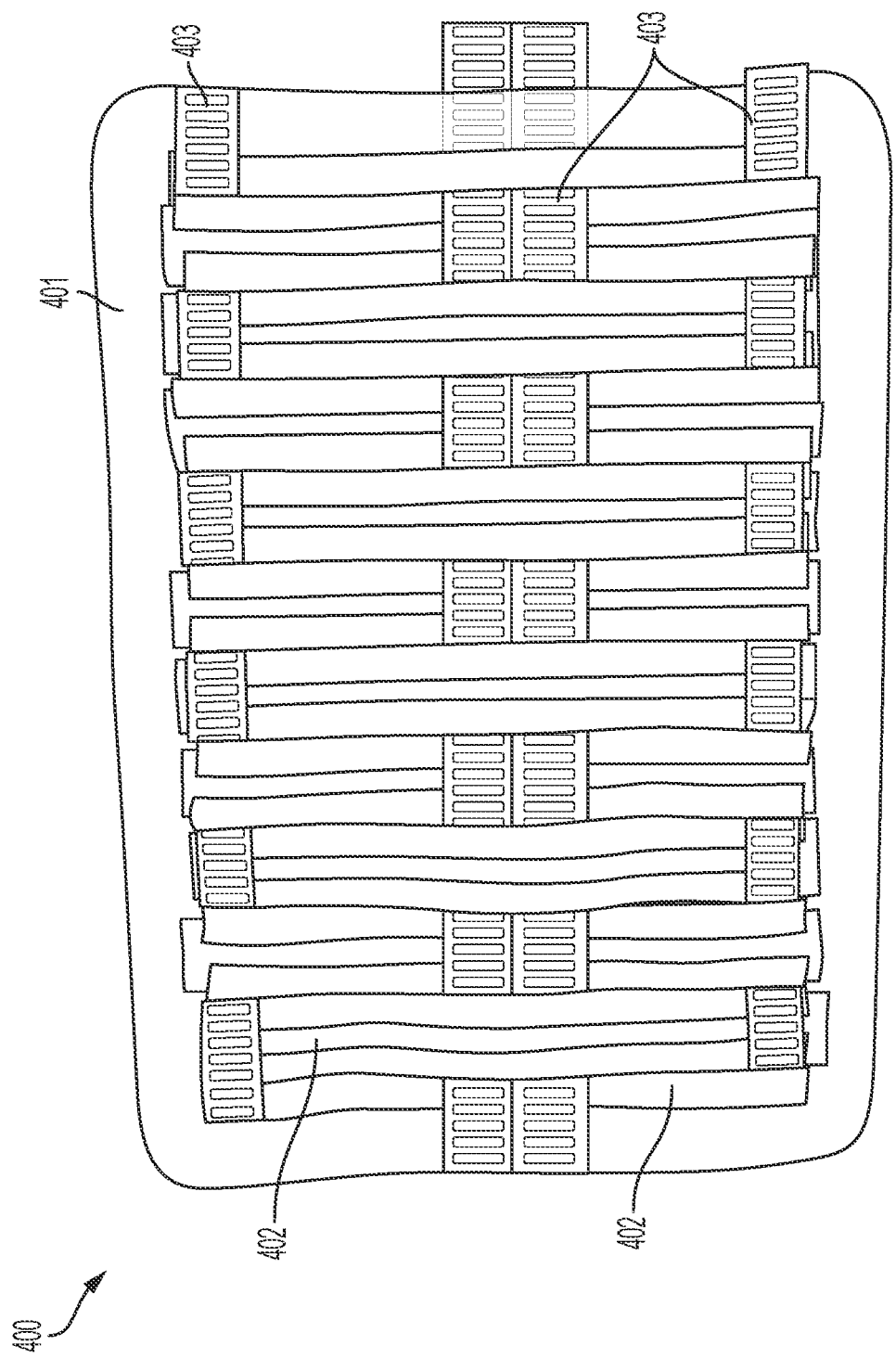
FIG. 4 illustrates process picture for constructing the knee sleeve depicting the protective material pattern and woven structure bands.

Further, the structure bands may be made from a durable material since the structure bands may also be subject to friction. The sleeve may include more than one support band. Specifically, the sleeve may include three support bands or support band sets. Each support band may be made of more than one support band. One of the support bands 403 may be located at the upper portion of the sleeve and, specifically, positioned at the top of the vertical cuts. Another of the support bands 403 may be located at the lower portion of the sleeve and, specifically, positioned at the bottom of the vertical cuts. A third of the support bands 403 may be located in a center portion of the sleeve. The structure bands may be weaved through the cuts in the base layer. This is illustrated in FIG. 4. The top support band and the bottom support band may be weaved in a matching weave pattern. In other words, they both may have, for example, an over, under, over, under, over, under weave pattern. The center support band may be weaved in an opposite weave pattern from the top and bottom support bands. In other words, using the example above, the center support band may have an under, over, under, over, under, over weave pattern. While the top and bottom support bands may be cut to be flush with the vertical edge of the base layer, the center support band may extend past the edge of the base layer to act as an additional attachment mechanism, as discussed further herein.

The support bands may be exposed to friction from either the prosthetic or the clothing material. Thus, the structure bands may be made of a durable material to withstand such influences of friction. For example, the structure bands may be elastic bands that are woven throughout the knee sleeve. Elastic bands permit expanding and contracting and may operate without notice alongside the motion of the user's knee. In other words, the use of the elastic bands allow the knee to move without a noticeable, additional force on the knee joint and provides an increase in structure. Additionally, elastic bands are generally strong and able to withstand friction forces to minimize wear on the sleeve. In an embodiment, the structure bands may be made from any material that permits the natural motion of a knee joint and has the durability to act as a support structure of the knee sleeve.

The knee sleeve apparatus may also include a protective sheet overlaying the protective material along the upper portion of the base material. The protective sheet (illustrated at 504 in FIG. 5) may be placed over the protective material and the base layer. In an embodiment, the protective sheet is durable material that contacts the edge of the prosthetic on the inside of the knee sleeve. The protective sheet is utilized to take the majority of the friction produced between the rubbing of the prosthetic and the knee sleeve. Thus, this portion may be manufactured to be easily removable so that it can be replaced when worn out. This extra layer of highly durable material may provide greater protection of the knee sleeve against the prosthetic friction.

The protective sheet may be a polycarbonate material. Polycarbonate is a durable material with a high friction resistance. The use of such polycarbonate may protect the protective material, and thereafter protect the base material from the friction between the prosthetic and the knee sleeve. In an embodiment, any highly durable material may be used as a protective sheet within the knee sleeve, as long as such material permits for the transition from a flat state (not in use) to a cylindrical state (in use). For example, a thick piece of sheet metal, though very durable, will not make an appropriate protection sheet for it is not easily maneuverable.

As mentioned previously with reference to FIG. 1, when securing the knee sleeve to a user, the user may establish at least two anchor points and utilize two or more straps to secure the knee sleeve to the user's leg. In an embodiment, when attaching the knee sleeve at the anchor points, the user may utilize a strap attached to the sleeve to wrap around the knee sleeve and, therefore, around the limb of the user. Thus, the sleeve may also include one or more attachment mechanisms that are coupled to the knee sleeve (illustrated at 701 and 702 in FIG. 7). Additionally, as previously mentioned, the center support band may extend past the edge of the base layer and a third attachment means may be added to the extra support band, thus allowing the center support band to act as a third attachment mechanism (illustrated at 603 in FIG. 6).

In an embodiment, the straps utilized may wrap around the designated anchor portion of the user's legs, and then use a mechanical mechanism to hold the strap in place, which results in holding the knee sleeve in place. The third attachment mechanism, if used, allows for connecting one side of the sleeve to the other side of the sleeve in the center, whereas the other two attachment mechanisms connect the sleeve together at the top and bottom of the sleeve. In an embodiment, the straps are made from a durable material, for example, a woven fabric, roller-blading straps, or the like. The straps may include the mechanical mechanism for connection of the two pieces and may be integrally coupled to the strap.

In an embodiment, the mechanical fastening mechanism may be a hook and loop fastener, a loop and tie fastener, a snap, a buckle, and/or the like. In certain fastening mechanism, other components may be utilized. For example, with a hook and loop fastener, the strap may include a buckle portion that the strap is looped through to allow for tightening the strap. After wrapping a strap around an anchor point, in an embodiment, the strap end may be reconnected to the knee sleeve device by use of the mechanical mechanism. For example, if a strap includes the mechanical mechanism of hook and loop fastener, upon wrapping the user's leg with a strap, the strap having the hook portion of the fastener may be reconnected to the portion of the knee sleeve having the loop portion of the fastener, and held in place. As another example, if the strap includes rollerblading straps and a loop and tie method, after the strap is wrapped around the user's leg, the loop and tie method permits that strap to be reconnected to the knee sleeve device, thereby securing the knee sleeve device in place over the knee joint. It should be noted that all of the components are mechanically coupled to the device, for example, using a sewing technique, a durable fastening technique (e.g., strong glue, heat coupling, etc.), or the like. The mechanically coupling technique may also allow for removal of some components where applicable, for example, the protective sheet.

Figure 3:
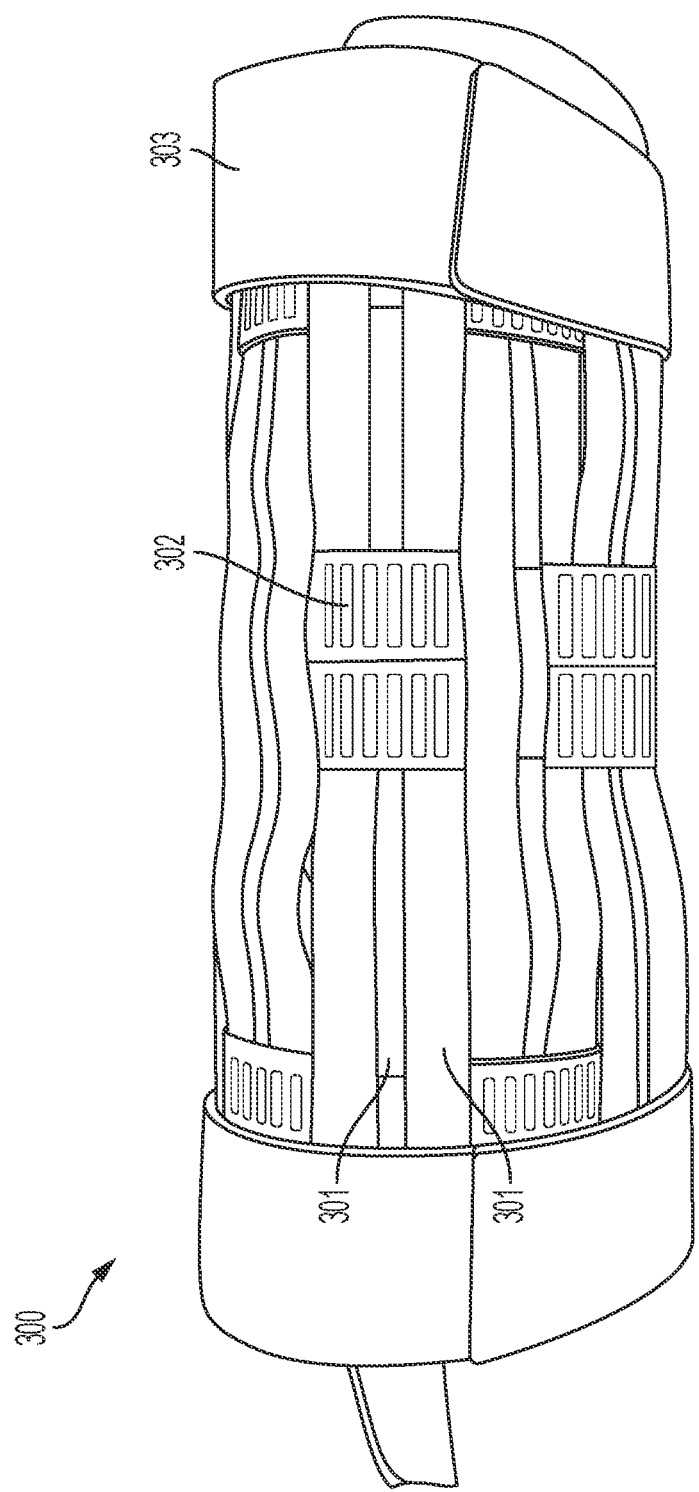
FIG. 3 illustrates a side view of the knee sleeve in the cylindrical, closed use.

FIG. 3 illustrates an example of a closed knee sleeve device, thus illustrating knee sleeve 300 in its cylindrical form as if the user was wearing the knee sleeve device. At 301, the protective material is being shown. In this example, the protective material is bias tape. It is important to remember that this is a non-limiting example, however, throughout this example, the protective material will be continually referenced to as bias tape. As can be seen in 300, there are two locations for 301. Both of these locations are pointing towards bias tape. The lighter color represents the strips that are located between the cuts of the base layer. The darker color represents the strips that are positioned to cover the edges of the cuts and, thus, are located on both the front and the back of the device.

302 are the woven structure bands present along the center portion of 300. As can be seen in 300, the woven portions of 302 are present over some bias tape 301 portions, and beneath others, exemplifying the woven method utilized. 303 illustrates the lower strap used to wrap around a determined anchor point on the prosthetic portion of the user's leg. This strap is made from a highly durable fabric material, and, in this example, utilizes hook and loop fastener as the mechanical mechanism holding the strap in place. Further, on the other side of 300, the upper strap is present and consists of the same material and mechanical mechanism of 303. These are non-limiting examples of materials used for the straps and mechanical mechanism. However, for ease of understanding, the highly durable fabric and hook and loop fastener may be referenced throughout the example figures.

In FIG. 4, 402 was previously referenced when discussing the pattern of the protective material and how the pattern encourages mobility and 403 was referenced when discussing the support bands. 400 illustrates the device during a point in the manufacturing process of the knee sleeve, where the base material 401 is still viewable, protective materials 402 have been added in a pattern, and structure bands 403 are shown to be weaved through the base layer and around the protective material. At 401, the base material is a polypropylene sheet with a mesh pattern which permits ease in mobility and is light, while maintaining a durable base. The protective material 402 is bias tape, and the structure bands 403 consist of highly durable fabric covered elastic bands, which, as discussed previously, provides a foundation to the knee sleeve and allows for seamless knee movement while remaining secure to the user's leg and cover their knee joint.

Figure 5:
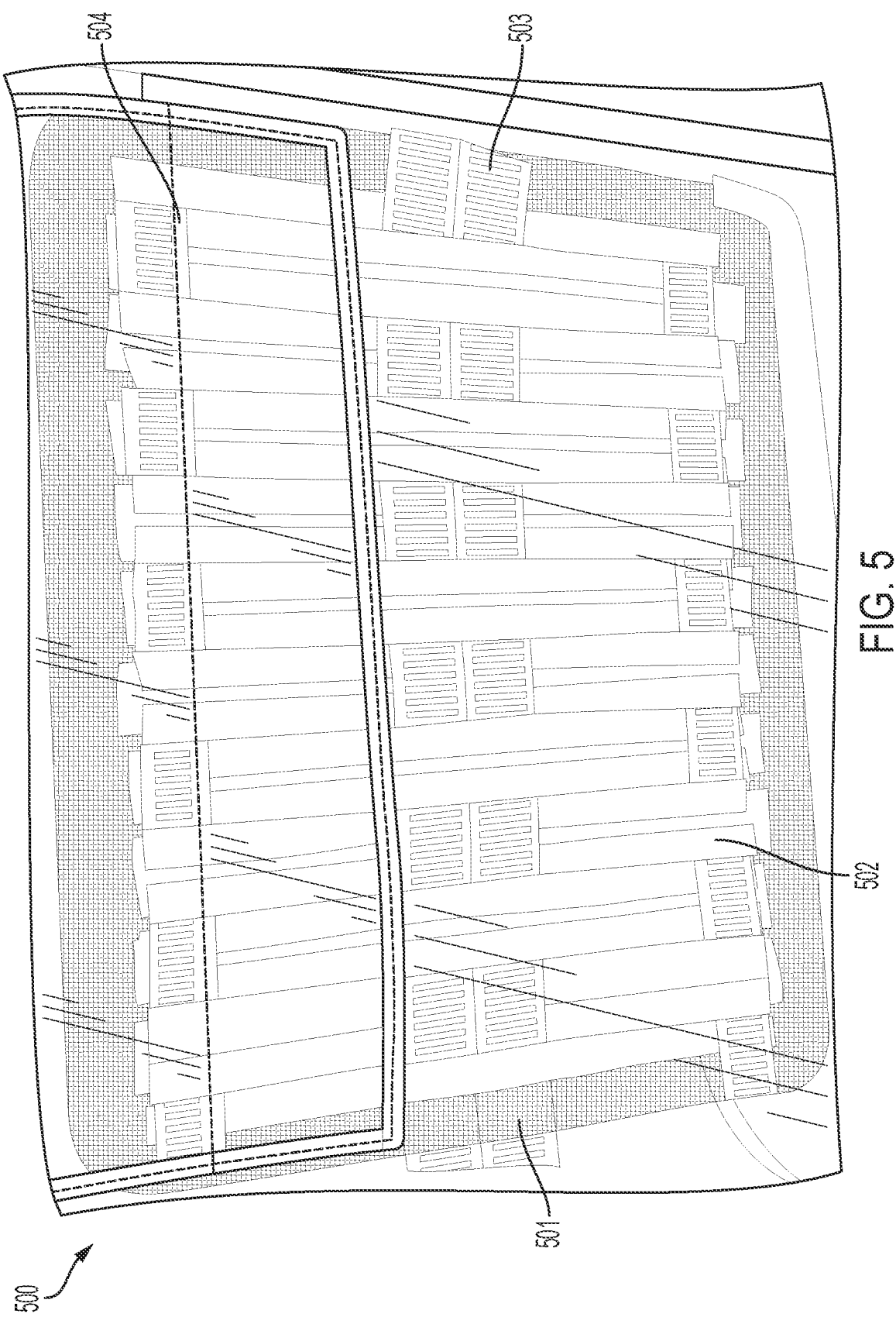
FIG. 5 illustrates an inside view of knee sleeve upon implementation of the protective sheet.

FIG. 5 shows an inside view of the knee sleeve during a step of manufacturing. 500 is a nearly completed knee sleeve; however, it is missing the straps. More importantly, 500 illustrates the protective sheet 504 overlaying the protective material along the upper portion of the material. 504 will be in direct contact with the edges of the prosthetic that may tear and rip through clothing if no sleeve is present. Thus, 504 provides an extra protective buffer along the inside of the knee sleeve. The protective sheet 504 is made from a polycarbonate sheet which is highly durable and permits the transition between a flat (opened) knee sleeve and a cylindrical (closed) knee sleeve. Similar to the previous figures, 500 includes 501 polypropylene sheet with a mesh pattern (base layer), 502 bias tape (protective material), and 503 durable fabric covered elastic bands (support band). As can be seen in 500, the size of 504 overlays the entire top portion width of the inside of the knee sleeve, and covers the bias tape 502 until reaching 503; thus, the entire top inner portion of the knee sleeve is reinforced. This protective sheet 504 may be attached in a manner that allows for it to be removed and replaced if it becomes worn.

Figure 6:
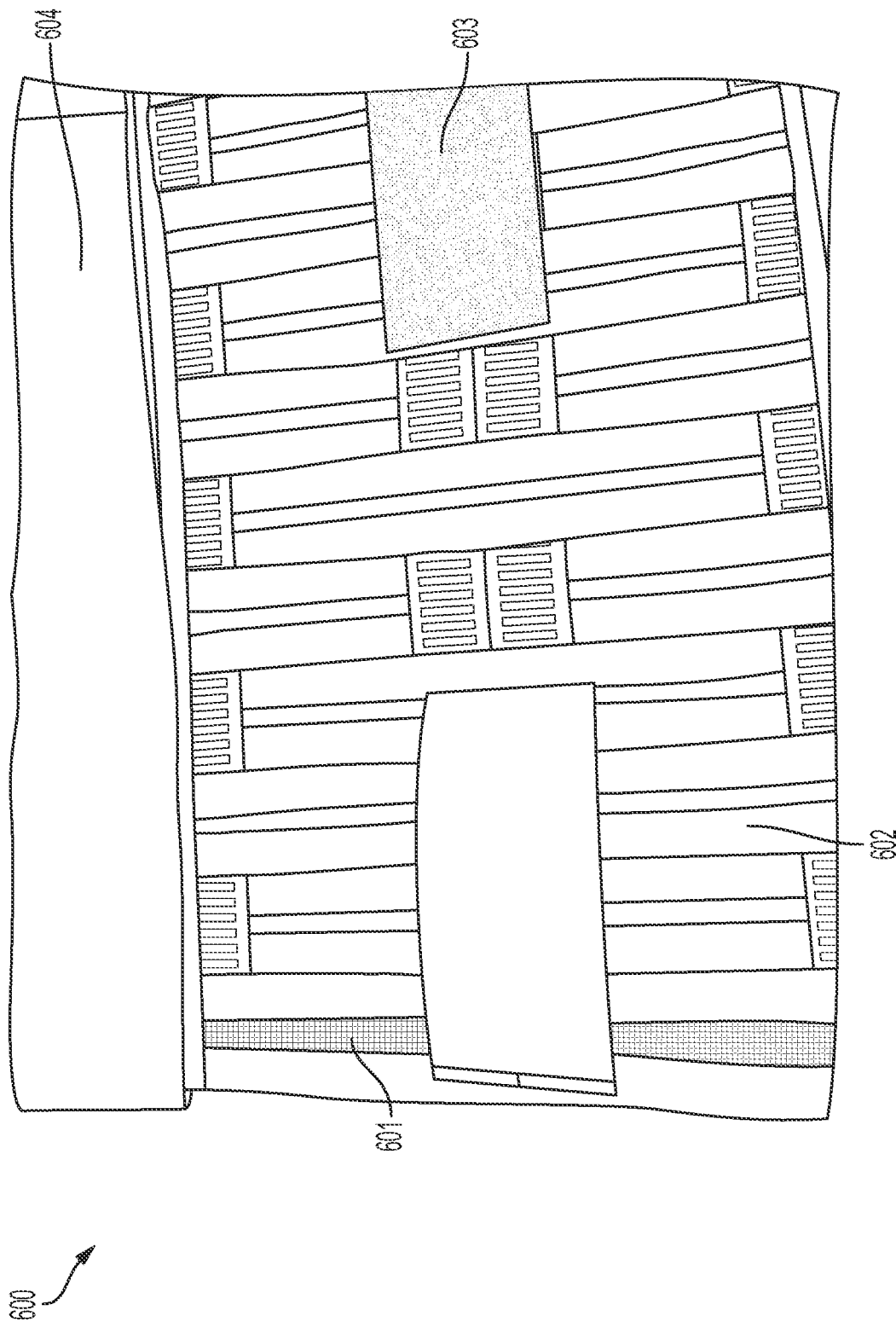
FIG. 6 illustrates a finished outside view of the knee sleeve and present components.
Figure 7:
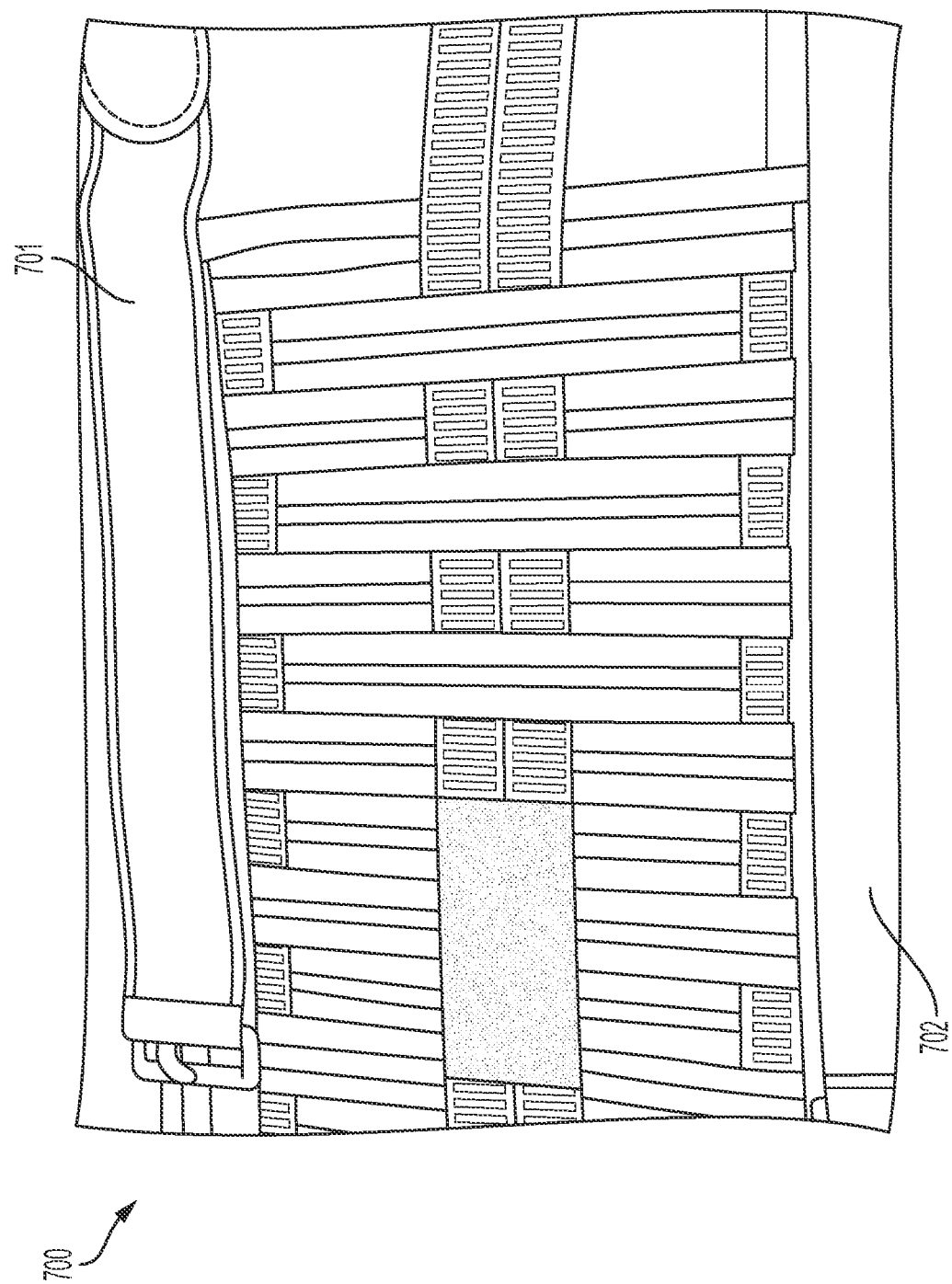
FIG. 7 illustrates a finished outside view of the knee sleeve with both straps and mechanical mechanism for connection.

FIG. 6 shows an outside view of the opened knee sleeve 600. As mentioned previously, polypropylene sheet with a mesh pattern makes up base layer 601. It is important to remember that in the final device, the polypropylene sheet with a mesh pattern 601 will not be viewable unless the knee sleeve is dismantled, for example, removing bias tape 602. 603 illustrates the durable fabric covered elastic bands and includes a fastener mechanism, and 604 represents the highly durable top fabric strap used to anchor and secure the knee sleeve to a user. FIG. 7 is continuation of FIG. 6. 700 is used to show that straps and mechanical mechanisms are present at both the top and bottom of knee sleeve 700. 701 illustrates the top strap with the hook and loop fastener present. The lower strap 702 is manufactured in a similar manner to the top strap 701.

This disclosure has been presented for purposes of illustration and description but is not intended to be exhaustive or limiting. Many modifications and variations will be apparent to those of ordinary skill in the art. The embodiments were chosen and described in order to explain principles and practical application, and to enable others of ordinary skill in the art to understand the disclosure for various embodiments with various modifications as are suited to the particular use contemplated.

Thus, although illustrative example embodiments have been described herein with reference to the accompanying figures, it is to be understood that this description is not limiting and that various other changes and modifications may be affected therein by one skilled in the art without departing from the scope or spirit of the disclosure.

What is claimed is:

1. An apparatus for protecting clothing from damage caused by a prosthetic device, comprising:
   a base material comprising a plurality of vertical cuts;
   a protective material covering a front and a back of the base material, wherein the protective material is fabric and allows access to the plurality of vertical cuts;
   one or more structure bands weaved through at least a subset of the plurality of vertical cuts;
   a protective sheet overlaying the protective material on the back of the base material and along an upper portion of the apparatus, wherein the protective sheet, when the apparatus is worn, contacts a portion of the prosthetic device worn by a user; and
   two or more straps coupled to the apparatus, wherein each of the two or more straps comprise a mechanical mechanism for securing the apparatus when worn by the user;
   wherein the securing the apparatus comprises wrapping one of the two or more straps around a lower portion of a limb of the user and wrapping another of the two or more straps around an upper portion of the prosthetic device worn by the user.

2. The apparatus of claim 1, wherein the base material is a polypropylene.

3. The apparatus of claim 2, wherein the polypropylene is a single sheet.

4. The apparatus of claim 1, wherein the one or more structure bands are elastic bands.

5. The apparatus of claim 1, wherein the protective sheet comprises a polycarbonate material.

6. The apparatus of claim 1, wherein the protective sheet is located on an inside portion of the apparatus.

7. The apparatus of claim 1, wherein the two or more straps are elastic bands.

8. The apparatus of claim 1, wherein the mechanical mechanism comprises a hook and loop fastener.

9. The apparatus of claim 1, wherein at least one of the one or more structure bands is weaved through an upper portion of the apparatus;
   wherein at least another one of the one or more structure bands is weaved through a lower portion of the apparatus, wherein a pattern of the weave of the at least another one of the one or more structure bands matches a pattern of the weave of the one of the one or more structure bands; and
   wherein at least a third one of the one or more structure bands is weaved through a central portion of the apparatus, wherein a pattern of the weave of the at least a third one of the one or more structure bands is opposite the pattern of weave of the at least another one of the one or more structure bands.

10. A device for protecting clothing from damage caused by a prosthetic device, the device comprising:
    a base layer comprising a plurality of cuts extending in a vertical direction from an upper portion of the base layer to a lower portion of the base layer, wherein the plurality of cuts do not extend from edge to edge;
    a first set of a plurality of strips of material located on a front side of the base layer, wherein each of the plurality of strips of the first set are positioned between two of the plurality of vertical cuts of the base layer;
    a second set of a plurality of strips of material located on a back side of the base layer, wherein each of the plurality of strips of the second set are positioned between two of the plurality of vertical cuts of the base layer;

at least one support band weaved through the plurality of vertical cuts and positioned at a top of the plurality of vertical cuts;

at least a second support band weaved through the plurality of vertical cuts and positioned at a bottom of the plurality of vertical cuts;

at least a third support band weaved through the plurality of vertical cuts and positioned at a center position of the plurality of vertical cuts;

at least one attachment mechanism positioned at an upper portion of the device, wherein the at least one attachment mechanism allows for attachment of the device to a limb of a user; and at least a second attachment mechanism positioned at a lower portion of the device, wherein the at least a second attachment mechanism allows for attachment of the device to a prosthetic of the user.

11. The device of claim 10, wherein the base material is a polypropylene.

12. The device of claim 10, comprising a third set of a plurality of strips of material positioned through the vertical cuts such that a portion of each of the plurality of strips is located on the front side of the base layer and another portion of each of the plurality of strips is located on the back side of the base layer.

13. The device of claim 10, wherein each of the first set of a plurality of strips of material and the second set of a plurality of strips of material comprise fabric.

14. The device of claim 10, wherein the at least a third support band extends past a vertical edge of the device and forms at least a part of an at least a third attachment mechanism.

15. The device of claim 10, further comprising a protective sheet positioned at an upper portion of a front side of the device.

16. The device of claim 10, wherein the protective sheet comprises a polycarbonate material.

17. The device of claim 10, wherein each of the at least one support band, the at least a second support band, and the at least a third support band comprise at least one elastic band.

18. The device of claim 10, wherein the at least one attachment mechanism comprises a mechanical mechanism and wherein the mechanical mechanism is a hook and loop fastener.

19. The device of claim 10, wherein a weave pattern of the at least one support band matches a weave pattern of the at least a second support band and wherein a weave pattern of the at least a third support band is opposite the weave pattern of the at least one support band and the at least a second support band.

* * * * *